(12) United States Patent
Gumaste et al.

(10) Patent No.: US 8,439,033 B2
(45) Date of Patent: May 14, 2013

(54) INHALATION DEVICE

(75) Inventors: Anand Gumaste, West Windsor, NJ (US); Henri Akouka, Moorestown, NJ (US)

(73) Assignee: Microdose Therapeutx, Inc., Monmouth Junction, NJ (US)

(*) Notice: Subject to any disclaimer, the term of this patent is extended or adjusted under 35 U.S.C. 154(b) by 1160 days.

(21) Appl. No.: 12/246,208

(22) Filed: Oct. 6, 2008

(65) Prior Publication Data

US 2009/0090361 A1    Apr. 9, 2009

Related U.S. Application Data

(60) Provisional application No. 60/978,672, filed on Oct. 9, 2007.

(51) Int. Cl.
*A61M 11/00* (2006.01)
(52) U.S. Cl.
USPC ............. 128/204.21; 128/204.26; 128/203.19
(58) Field of Classification Search ............. 128/204.21, 128/203.12, 204.23, 204.26, 203.25, 203.19
See application file for complete search history.

(56) References Cited

U.S. PATENT DOCUMENTS

| | | | |
|---|---|---|---|
| 1,419,618 A | 6/1922 | Deming | 424/438 |
| 1,580,576 A | 4/1926 | Weidner | 510/146 |
| 2,102,885 A | 12/1937 | Carroll | 206/530 |
| 2,340,037 A | 1/1944 | Zipper | 424/453 |
| 2,517,482 A | 4/1949 | Hall | |
| 3,048,526 A | 8/1962 | Boswell | 424/472 |
| 3,241,625 A | 3/1966 | Soojian | 177/120 |
| 3,507,277 A | 9/1967 | Altounyan et al. | |
| 3,518,992 A | 9/1967 | Altounyan et al. | |
| 3,437,074 A | 4/1969 | Hagopain et al. | 118/623 |
| 3,620,759 A | 11/1971 | Maddox | 426/78 |
| 3,635,219 A | 1/1972 | Altounyan et al. | |
| 3,702,653 A | 11/1972 | Motten | 206/534 |
| 3,795,244 A | 3/1974 | Lax et al. | |
| 3,807,400 A | 4/1974 | Cocozza | |
| 3,831,606 A | 8/1974 | Damani | |
| D235,215 S | 5/1975 | Larson | D24/104 |
| 3,889,636 A | 6/1975 | Smith | 118/621 |
| 3,943,437 A | 3/1976 | Mourier | 324/32 |
| 3,977,323 A | 8/1976 | Pressman et al. | 101/426 |

(Continued)

FOREIGN PATENT DOCUMENTS

| | | |
|---|---|---|
| CA | 2 451 519 | 9/2003 |
| DE | 102005005540 | 8/2006 |

(Continued)

OTHER PUBLICATIONS

Translation of Examination Report filed in Pakistan, Appln. No. 1172/2008, dated Feb. 23, 2012 (1 pg).

(Continued)

*Primary Examiner* — Steven Douglas
(74) *Attorney, Agent, or Firm* — Hayes Soloway P.C.

(57) ABSTRACT

A dry inhaler system includes a vibrating mechanism. A supply of a dry powder is operatively coupled to the vibrating mechanism. A power source communicates with the vibrating mechanism. A sensor communicates with the vibrating mechanism. A feedback control communicates with the sensor and the power source. The feedback control controls power delivered to the vibrating mechanism relative to information provided by the sensor about the performance of the vibrating mechanism.

8 Claims, 3 Drawing Sheets

U.S. PATENT DOCUMENTS

| | | | | |
|---|---|---|---|---|
| 3,999,119 | A | 12/1976 | Bares | 324/32 |
| 4,021,587 | A | 5/1977 | Banker | 427/18 |
| 4,069,084 | A | 1/1978 | Mlodozeniec et al. | 156/378 |
| 4,071,169 | A | 1/1978 | Dunn | 222/76 |
| 4,182,447 | A | 1/1980 | Kay | 206/220 |
| 4,196,564 | A | 4/1980 | Bodenmann et al. | 53/471 |
| 4,196,565 | A | 4/1980 | Bodenmann et al. | 53/471 |
| 4,197,289 | A | 4/1980 | Sturzenegger et al. | 424/21 |
| 4,204,766 | A | 5/1980 | Harada | 356/404 |
| D258,091 | S | 1/1981 | Reed et al. | D24/101 |
| 4,247,006 | A | 1/1981 | Bodenmann et al. | 206/528 |
| 4,250,997 | A | 2/1981 | Bodenmann et al. | 206/528 |
| 4,252,434 | A | 2/1981 | Nakamura et al. | 355/15 |
| 4,255,777 | A | 3/1981 | Kelly | 361/228 |
| 4,339,428 | A | 7/1982 | Tencza | 424/21 |
| 4,349,531 | A | 9/1982 | Mlodozeniec et al. | 424/27 |
| 4,376,111 | A | 3/1983 | Tovey | 424/467 |
| 4,379,969 | A | 4/1983 | Cobb et al. | 250/324 |
| D269,718 | S | 7/1983 | Tovey | D24/101 |
| D269,721 | S | 7/1983 | Tovey | D24/101 |
| D269,722 | S | 7/1983 | Tovey | D24/101 |
| 4,399,699 | A | 8/1983 | Fujishiro | 73/304 |
| D274,846 | S | 7/1984 | Eoga | D24/101 |
| 4,514,781 | A | 4/1985 | Plasschaert et al. | 361/230 |
| 4,555,174 | A | 11/1985 | Kramer | 355/3 DD |
| D283,649 | S | 4/1986 | Casberg | D23/207 |
| 4,594,901 | A | 6/1986 | Norman | 73/861.04 |
| 4,601,896 | A | 7/1986 | Nugent | 424/453 |
| D285,363 | S | 8/1986 | Tovey | D24/101 |
| D286,085 | S | 10/1986 | Tovey | D24/101 |
| 4,626,876 | A | 12/1986 | Miyagawa et al. | 346/160 |
| 4,643,731 | A | 2/1987 | Eckenhoff | 604/892.1 |
| 4,733,797 | A | 3/1988 | Haber | 221/8 |
| 4,734,722 | A | 3/1988 | Maczuszenko et al. | 346/159 |
| 4,735,805 | A | 4/1988 | Ni et al. | 424/464 |
| 4,772,470 | A | 9/1988 | Inoue et al. | |
| 4,795,644 | A | 1/1989 | Zentner | 424/468 |
| 4,848,267 | A | 7/1989 | Slayton et al. | 118/653 |
| 4,875,060 | A | 10/1989 | Masuda et al. | 346/155 |
| 4,878,454 | A | 11/1989 | Cann | 118/663 |
| 4,883,182 | A | 11/1989 | Hughes | 206/534 |
| 5,005,516 | A | 4/1991 | Speer | 118/657 |
| 5,009,894 | A | 4/1991 | Hsiao | 424/451 |
| 5,055,306 | A | 10/1991 | Barry et al. | 424/482 |
| 5,074,426 | A | 12/1991 | Goodhart et al. | 220/4.24 |
| 5,075,114 | A | 12/1991 | Roche | |
| 5,102,045 | A | 4/1992 | Diana | 239/3 |
| 5,129,572 | A | 7/1992 | Keilberth et al. | 228/131 |
| 5,204,055 | A | 4/1993 | Sachs et al. | 419/2 |
| 5,207,705 | A | 5/1993 | Trudell et al. | |
| 5,214,386 | A | 5/1993 | Singer et al. | 324/452 |
| 5,344,043 | A | 9/1994 | Moulding et al. | 221/71 |
| 5,404,871 | A | 4/1995 | Goodman et al. | 128/200.14 |
| 5,417,980 | A | 5/1995 | Goldman et al. | |
| 5,421,816 | A | 6/1995 | Lipkovker | 604/20 |
| 5,454,271 | A | 10/1995 | Yamamoto et al. | 73/861.04 |
| 5,487,901 | A | 1/1996 | Conte et al. | |
| 5,490,962 | A | 2/1996 | Cima et al. | 264/22 |
| 5,508,040 | A | 4/1996 | Chen | 424/451 |
| D376,643 | S | 12/1996 | Hatton et al. | D24/101 |
| 5,629,316 | A | 5/1997 | Kurihara et al. | 514/263.32 |
| 5,655,523 | A | 8/1997 | Hodson et al. | 128/315 |
| 5,669,973 | A | 9/1997 | Pletcher | 118/624 |
| 5,672,359 | A | 9/1997 | Digenis et al. | 424/463 |
| 5,699,649 | A | 12/1997 | Abrams et al. | 53/428 |
| 5,714,007 | A | 2/1998 | Pletcher et al. | 118/629 |
| 5,827,538 | A | 10/1998 | Cussler et al. | 424/473 |
| 5,858,099 | A | 1/1999 | Sun et al. | 118/621 |
| 5,884,624 | A | 3/1999 | Barnett et al. | 128/206.24 |
| 5,906,202 | A | 5/1999 | Schuster et al. | 128/203.23 |
| 5,960,609 | A | 10/1999 | Abrams et al. | 53/428 |
| 6,009,690 | A | 1/2000 | Rosenberg et al. | 53/454 |
| 6,013,280 | A | 1/2000 | Frisbee et al. | 424/464 |
| D420,464 | S | 2/2000 | Binstock et al. | D28/8.1 |
| 6,026,809 | A * | 2/2000 | Abrams et al. | 128/203.15 |
| 6,027,748 | A | 2/2000 | Conte et al. | 424/458 |
| 6,032,871 | A | 3/2000 | Borner et al. | 239/3 |
| 6,074,688 | A | 6/2000 | Pletcher et al. | 427/2.14 |
| 6,136,344 | A | 10/2000 | Depui et al. | |
| 6,152,130 | A * | 11/2000 | Abrams et al. | 128/204.21 |
| 6,153,218 | A | 11/2000 | Barnwell et al. | |
| 6,197,331 | B1 | 3/2001 | Lerner et al. | 424/448 |
| 6,319,541 | B1 | 11/2001 | Pletcher et al. | 427/2.14 |
| 6,350,468 | B1 | 2/2002 | Sanso | 424/456 |
| 6,367,470 | B1 | 4/2002 | Denyer et al. | 128/200.14 |
| 6,428,809 | B1 | 8/2002 | Abrams et al. | 424/451 |
| 6,629,646 | B1 | 10/2003 | Ivri | 239/4 |
| 6,702,683 | B2 | 3/2004 | Abrams et al. | |
| 6,869,615 | B2 | 3/2005 | Chen et al. | |
| 6,889,690 | B2 | 5/2005 | Crowder et al. | 128/203.15 |
| 6,971,383 | B2 * | 12/2005 | Hickey et al. | 128/203.15 |
| 6,978,779 | B2 * | 12/2005 | Haveri | 128/200.16 |
| D520,635 | S | 5/2006 | Bonny et al. | D24/104 |
| D530,814 | S | 10/2006 | Bonny et al. | D24/104 |
| 7,118,010 | B2 | 10/2006 | Crowder et al. | |
| D535,741 | S | 1/2007 | Stawski et al. | D24/101 |
| 7,233,228 | B2 | 6/2007 | Lintell | 340/309.7 |
| D556,946 | S | 12/2007 | Seum | |
| D564,086 | S | 3/2008 | Nielsen et al. | |
| 7,538,473 | B2 | 5/2009 | Blandino et al. | 310/317 |
| 7,607,435 | B2 | 10/2009 | Lipp | 128/203.13 |
| 7,748,382 | B2 | 7/2010 | Denyer et al. | 128/204.21 |
| 2002/0032409 | A1 | 3/2002 | Ritsche | 604/154 |
| 2004/0050860 | A1 | 3/2004 | Crowder et al. | 222/1 |
| 2004/0142036 | A1 | 7/2004 | Abrams et al. | |
| 2004/0156903 | A1 | 8/2004 | Abrams et al. | |
| 2004/0185100 | A1 | 9/2004 | Franz | 424/472 |
| 2004/0224020 | A1 | 11/2004 | Schoenhard | 424/471 |
| 2004/0250812 | A1 | 12/2004 | Davies et al. | 128/200.14 |
| 2005/0008690 | A1 | 1/2005 | Miller | 424/451 |
| 2005/0053649 | A1 | 3/2005 | Chalmers | 424/451 |
| 2005/0121027 | A1 | 6/2005 | Nilsson et al. | 128/200.23 |
| 2005/0155601 | A1 | 7/2005 | Steiner et al. | 128/200.23 |
| 2005/0174216 | A1 | 8/2005 | Lintell | 340/309.16 |
| 2005/0183725 | A1 | 8/2005 | Gumaste et al. | 128/203.15 |
| 2005/0267628 | A1 | 12/2005 | Crowder et al. | 700/240 |
| 2006/0191534 | A1 | 8/2006 | Hickey et al. | 128/203.15 |
| 2006/0213503 | A1 | 9/2006 | Borgschulte et al. | 128/200.14 |
| 2006/0257327 | A1 | 11/2006 | Zierenberg et al. | 424/46 |
| 2007/0087048 | A1 | 4/2007 | Abrams et al. | |
| 2007/0137645 | A1 | 6/2007 | Eason et al. | 128/203.15 |
| 2009/0020113 | A1 | 1/2009 | Watanabe | 128/200.14 |
| 2009/0308390 | A1 | 12/2009 | Smutney et al. | 128/203.15 |
| 2010/0139654 | A1 | 6/2010 | Thoemmes et al. | 128/203.15 |
| 2010/0252032 | A1 | 10/2010 | Thoemmes et al. | 128/200.23 |
| 2011/0041844 | A1 | 2/2011 | Dunne | 128/203.12 |

FOREIGN PATENT DOCUMENTS

| | | |
|---|---|---|
| DE | 102009005048 | 7/2010 |
| EP | 0 308 637 | 4/1988 |
| EP | 0431924 | 1/1996 |
| EP | 0885662 | 12/1998 |
| EP | 0891817 | 1/1999 |
| EP | 1 499 276 | 1/2005 |
| EP | 0 799 076 | 3/2005 |
| EP | 1 124 602 | 4/2005 |
| EP | 1 534 366 | 6/2005 |
| EP | 1 617 820 | 1/2006 |
| EP | 1 691 781 | 8/2006 |
| EP | 1 713 530 | 10/2006 |
| EP | 1 986 721 | 11/2008 |
| EP | 1 581 291 | 1/2009 |
| EP | 2 054 167 | 5/2009 |
| EP | 1 292 347 | 10/2009 |
| EP | 1 691 783 | 11/2009 |
| EP | 2 162 174 | 3/2010 |
| EP | 2 016 965 | 5/2010 |
| EP | 2 047 881 | 8/2010 |
| EP | 2 234 728 | 10/2010 |
| EP | 1 706 099 | 5/2011 |
| JP | 4277126 | 10/1992 |
| JP | 2000-503866 | 4/2000 |
| JP | 2005-536415 | 12/2005 |
| JP | 2007-523700 | 8/2007 |
| RU | 2286784 | 4/2005 |
| WO | WO 95/16438 | 6/1995 |
| WO | WO 9725065 | 7/1997 |

| WO | WO 9800337 | 1/1998 |
| WO | WO 98/36770 | 8/1998 |
| WO | WO 98/42446 | 10/1998 |
| WO | WO 99/30693 | 6/1999 |
| WO | WO 01/52815 | 7/2001 |
| WO | WO 02/096347 | 5/2002 |
| WO | WO 02/96347 | 5/2002 |
| WO | WO 03/092576 | 11/2003 |
| WO | WO 2004/002394 | 1/2004 |
| WO | WO 2004/093848 | 11/2004 |
| WO | WO 2005/053646 | 6/2005 |
| WO | WO 2005/074455 | 8/2005 |
| WO | WO 2007/096111 | 8/2007 |
| WO | WO 2008/021281 | 2/2008 |
| WO | WO 2009/007068 | 1/2009 |
| WO | WO 2009/090084 | 7/2009 |
| WO | WO 2011/160932 | 12/2011 |
| WO | WO 2011/163272 | 12/2011 |

OTHER PUBLICATIONS

Office Action in re. Chilean Application Serial No. 2989-2008 dated Mar. 17, 2010.

Invitation to Respond to Written Opinion/Written Opinion issued in Singapore Application Serial No. 201002452-9, dated Jul. 7, 2011 (16 pages).

Israel Official Action, Appln. No. 204955, dated Jun. 14, 2011 (1 page) and translation (1 page).

Sucker et al., "Feste orale and perorate Arzneiformen", Pharmazeutische Technologie, No. 2, 1991. p. 326, XP00214673.

Science News, vol. 151, p. 205, "Ink Jets not just for the Printed Page", Apr. 5, 1997.

U.S. Appl. No. 60/727,029, filed Oct. 14, 2005, Microdose Technologies, Inc.

Chile Official Action + Translation, dated Jan. 3, 2011 (7 pgs).

Translation of Official Action issued in Saudi Arabian Application Serial No. 08290609.

Chinese Office Action with English translation, Appln. No. 200880110921.6, dated Feb. 29, 2012 (17 pgs).

Peruvian Office Action, Appln. No. 1741-2008, Mar. 20, 2012 (4 pgs).

Russian Office Action w/translation, Appln. No. 2010118480, Jun. 20, 2012 (5 pgs).

Peruvian Office Action w/translation, Appln. No. 001741-2008, Aug. 17, 2012 (5 pgs).

Japanese Office Action with translation, Patent Appln. No. 2010-529010, dated Jan. 28, 2013, 6 pgs.

Australian Patent Modified Examination Report No. 1, issued in corresponding application No. 2008310916, dated Mar. 19, 2013 (4 pgs).

* cited by examiner

```
                    200
                      ↘

┌─────────────────────────────────────────────┐
    │ A vibrating mechanism is driven to an       │── 202
    │ approximate steady state using a first      │
    │ power input                                 │
    └─────────────────────────────────────────────┘
                      │
    ┌─────────────────────────────────────────────┐
    │ The first power input is removed, wherein   │── 204
    │ a vibration of at least a portion of the    │
    │ vibrating mechanism continues               │
    └─────────────────────────────────────────────┘
                      │
    ┌─────────────────────────────────────────────┐
    │ The vibration of the vibrating mechanism    │── 206
    │ is sensed after the voltage input is        │
    │ removed                                     │
    └─────────────────────────────────────────────┘
                      │
    ┌─────────────────────────────────────────────┐
    │ The steps of driving, removing, and sensing │── 208
    │ with a plurality of different power inputs  │
    │ are repeated                                │
    └─────────────────────────────────────────────┘
                      │
    ┌─────────────────────────────────────────────┐
    │ The voltage input that produced a largest   │── 210
    │ sensed vibration is determined              │
    └─────────────────────────────────────────────┘
                      │
    ┌─────────────────────────────────────────────┐
    │ The vibrating mechanism is positioned to    │── 212
    │ disaggregate the dry powder                 │
    └─────────────────────────────────────────────┘
```

FIG. 3

INHALATION DEVICE

CROSS REFERENCE TO RELATED APPLICATION

This application claims priority from U.S. Provisional Application Ser. No. 60/978,672, filed Oct. 9, 2007, the contents of which are incorporated herein in their entirety, by reference.

FIELD OF THE INVENTION

The present invention relates generally to the field of inhalation devices, and more specifically, to inhalation devices that utilize vibration to facilitate suspension of powder (e.g., powdered medication) into an inhaled gas stream (e.g., of inhaled air).

BACKGROUND OF THE INVENTION

Certain diseases of the respiratory tract are known to respond to treatment by the direct application of therapeutic agents. As these agents are most readily available in dry powdered form, their application is most conveniently accomplished by inhaling the powdered material through the nose or mouth. This powdered form results in the better utilization of the medicament in that the drug is deposited exactly at the site desired and where its action may be required; hence, very minute doses of the drug are often equally as efficacious as larger doses administered by other means, with a consequent marked reduction in the incidence of undesired side effects and medicament cost. Alternatively, the drug in this form may be used for treatment of diseases other than those of the respiratory system. When the drug is deposited on the very large surface areas of the lungs, it may be very rapidly absorbed into the blood stream; hence, this method of application may take the place of administration by injection, tablet, or other conventional means.

It is the opinion of the pharmaceutical industry that the bioavailability of the drug is optimum when the drug particles delivered to the respiratory tract are between 1 to 5 microns in size. When the drug particles need to be in this size range the dry powder delivery system needs to address a number of issues:

(1) Small size particles develop an electrostatic charge on themselves during manufacturing and storage. This causes the particles to agglomerate or aggregate, resulting in clusters of particles which have an effective size greater than 5 microns. The probability of these large clusters making it to the deep lungs then decreases. This in turn results in a lower percentage of the packaged drug being available to the patient for absorption.

(2) The amount of active drug that needs to be delivered to the patient may be of the order of 10s of micrograms. For example, albuterol, in the case of a drug used in asthma, this is usually 25 to 50 micrograms. Current manufacturing equipment can effectively deliver aliquots of drugs in milligram dose range with acceptable accuracy. So the standard practice is to mix the active drug with a filler or bulking agent such as lactose. This additive also makes the drug "easy to flow". This filler is also called a carrier since the drug particles also stick to these particles through electrostatic or chemical bonds. These carrier particles are very much larger than the drug particles in size. The ability of the dry powder inhaler to separate drug from the carrier is an important performance parameter in the effectiveness of the design.

(3) Active drug particles with sizes greater than 5 microns will be deposited either in the mouth or throat. This introduces another level of uncertainty since the bioavailability and absorption of the drug in these locations is different from the lungs. Dry powder inhalers need to minimize the drug deposited in these locations to reduce the uncertainty associated with the bioavailability of the drug.

Prior art dry powder inhalers (DPIs) usually have a means for introducing the drug (active drug plus carrier) into a high velocity air stream. The high velocity air stream is used as the primary mechanism for breaking up the cluster of micronized particles or separating the drug particles from the carrier. Several inhalation devices useful for dispensing this powder form of medicament are known in the prior art. For example, in U.S. Pat. Nos. 3,507,277; 3,518,992; 3,635,219; 3,795,244; and 3,807,400, inhalation devices are disclosed having means for piercing of a capsule containing a powdered medicament, which upon inhalation is drawn out of the pierced capsule and into the user's mouth. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, a device is disclosed having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced holes and into the inhaled air stream. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air.

These prior art devices present several problems and possess several disadvantages that are remedied by the inhalation devices of the present invention. For instance, these prior art devices require that the user exert considerable effort in inhalation to effect dispensing or withdrawal of powder from a pierced capsule into the inhaled air stream. With these prior art devices, suction of powder through the pierced holes in the capsule caused by inhalation generally does not withdraw all or even most of the powder out of the capsule, thus causing a waste of the medicament. Also, such prior art devices result in uncontrolled amounts or clumps, of powdered material being inhaled into the user's mouth, rather than a constant inhalation of controlled amounts of finely dispersed powder.

Known prior art includes a device for facilitating inhalation of a powdered medication that includes a body portion having primary and secondary air inlet channels and an outlet channel. The secondary inlet channel provides an enclosure for a capsule containing the powdered medication and the outlet channel is formed as a mouthpiece protruding from the body. A capsule piercing structure is provided, which upon rotation puts one or more holes in the capsule so that upon vibration of the capsule by an electro-mechanical vibrator, the powdered drug many be released from the capsule. The piercing means disclosed in Wilke et al includes three radially mounted, spring-biased piercing needles mounted in a trochoidal chamber. Upon hand rotation of the chamber, simultaneous inward radial motion of the needles pierces the capsule. Further rotation of the chamber allows the needles to be retracted by their spring mountings to their original positions to withdraw the needles from the capsule.

The electromechanical vibrator includes, at its innermost end, a vibrating plunger rod which projects into the intersection of the inlet channel and the outlet channel. Connected to the plunger rod is a mechanical solenoid buzzer for energizing the rod to vibrate. The buzzer is powered by a high energy electric cell and is activated by an external button switch. Upon inhalation through an outlet channel and concurrent pressing of a switch to activate the electromechanical vibrating means, air is sucked through inlet channels and the air stream through the secondary inlet channel raises the capsule up against the vibrating plunger rod. The capsule is thus vibrated rapidly with powder being fluidized and dispensed from the pierced holes therein. This technique is commonly used in manufacturing for dispensing powder through a hopper where the hopper is vibrated to fluidize the powder and move it through the hopper outlet. The pierced holes in the capsule represent the hopper outlet. The air stream through the inlet channel and aids in withdrawal of powder from the capsule and carries this powder through the outlet channel to the mouth of the user. The electromechanical vibrator means may be placed at a right angle to the inlet chamber and the amplitude and frequency of vibration may be altered to regulate dispensing characteristics of the inhaler.

Thus, as noted above, the vibrator's inhaler is an electromechanical device consisting of a rod driven by a solenoid buzzer. This electromechanical means may be a motor driving a cam. A disadvantage of the inhaler implementation is the relatively large mechanical movement required of the rod to effectively vibrate the capsule. The large movement of the rod, usually around 100s of microns, is necessary due to the elasticity of the capsule walls and inertia of the drug and capsule.

Moreover, solenoid buzzers typically have operating frequencies less than 5 Khz. This operating frequency tends to be noisy and therefore is not desirable when incorporated into a dry powder inhaler from a patient's perspective. A further disadvantage of the electrochemical actuators is a requirement for a high energy source, thus requiring a large battery source or frequent changes of the battery pack for portable units. Both these features are not desirable from a patient safety and "ease of use" standpoint.

The inhaler is primarily intended to reduce the amount of powder left behind in the capsule relative to other inhalers cited in the patent disclosure. However, the above-described device does not disaggregate the powder into particle sizes or groups less than 6 microns in size as is required for effective delivery of the medication to the lungs; rather, like the prior art inhalers, it continues to rely on an air stream velocity to disaggregate the powder ejected into the air stream, into particle sizes suitable for delivery to the lungs.

In another prior art inhalation device, a liquid medication is atomized by an ultrasonic device such as a piezo element. A stream of air, usually at a high velocity, or a propellant then carries the atomized particles to the patient. The energy required to atomize the liquid medication in the nebulizer is prohibitively high, making this approach for the delivery of drugs to the lungs only feasible as a desk top unit. The high voltage requirements to drive the piezo, to produce the necessary mechanical displacements, also severely effects the weight and size of the device. It is also not obvious that the nebulizer operating principles can be applied to the dry powder inhalers for delivery or powder medication to the lungs.

The prior art devices therefore have a number of disadvantages which makes them less than desirable for the delivery of dry powder to the lungs. Some of these disadvantages are:

The performance of the prior art inhalers depends on the flow rate generated by the user. Lower flow rate does not result in the powder being totally disaggregated and hence adversely affects the dose delivered to the patient.

Inconsistency in the bioavailability of the drugs from dose-to-dose because of lack of consistency in the disaggregation process.

Large energy requirements for driving the electromechanical based inhalers which increases the size of the devices making them unsuitable for portable use.

Yet another prior art device includes an inhaler that utilizes vibration to facilitate suspension of powder into a gas that overcomes the aforesaid and other disadvantages and drawbacks of the above prior art. More particularly, the inhaler of the includes a piezoelectric vibrator for vibrating the powder. A controller is provided for controlling supply (i.e., amplitude and/or frequency) of actuating electricity to the vibrator so as to cause vibration of the powder that is adapted to optimally suspend at least a portion of the powder into the gas. The controller may include a user-actuable control for permitting the user to select the vibration frequencies and/or amplitudes for optimally suspending in the gas the type of powder currently being used in the inhaler. The user-actuable control is pre-calibrated with the controller to cause the controller to adjust the frequency and/or amplitude of actuating electricity supplied to the vibrator to be that necessary for vibrating the type of powder selected by the user-actuable control in such a way as to optimally suspend at least a portion of the powder into the gas. The user-actuable control may include selection gradations in terms of the average size of the powder particles to be suspended in the gas, and/or in terms of desired vibration frequencies and amplitudes. Typically, vibration frequency should be adjusted to at least about 12 KHz, in order to optimally suspend such commonly used powdered medications in the gas vibration frequency and amplitude may be adjusted to optimize suspension of the particular powdered medication being used.

SUMMARY OF THE INVENTION

The present invention provides improvements over prior art inhalers incorporating piezoelectric vibrators such as described above. More particularly, we have observed that excessive displacement is directly related to premature failure of piezoelectric transducers. Thus, it would be beneficial to have feedback regarding transducer displacement during the operation of the dry powder inhaler devices. Piezoelectric ceramics, having a bidirectional relationship between mechanical force and voltage, could be used simultaneously as a driving and feedback device. However, in a small, low cost device, secondary feedback systems would be prohibitively large and expensive. The present invention provides such feedback.

Embodiments of the present invention provide a system and method for providing a dry powder inhaler. Briefly described, in architecture, one embodiment of the system, among others, can be implemented as follows. The system includes a vibrating mechanism. A supply of a dry powder is operatively coupled to the vibrating mechanism. A power source communicates with the vibrating mechanism. A sensor communicates with the vibrating mechanism. A feedback control communicates with the sensor and the power source. The feedback control controls power delivered to the vibrating mechanism relative to information provided by the sensor about the performance of the vibrating mechanism.

The present invention can also be viewed as providing methods for providing feedback control for a dry powder inhaler. In this regard, one embodiment of such a method, among others, can be broadly summarized by the following steps: driving a vibrating mechanism to an approximate steady state using a first power input; removing the first power input, wherein a vibration of at least a portion of the vibrating mechanism continues; sensing the vibration of the vibrating mechanism after the voltage input is removed; repeating the steps of driving, removing, and sensing with a plurality of different power inputs; determining which of the voltage inputs produced a largest sensed vibration; and positioning the vibrating mechanism to disaggregate the dry powder.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 3 is a flowchart illustrating a method of providing the abovementioned dry powder inhaler, in accordance with the first exemplary embodiment of the invention.

DETAILED DESCRIPTION

Figure 1:
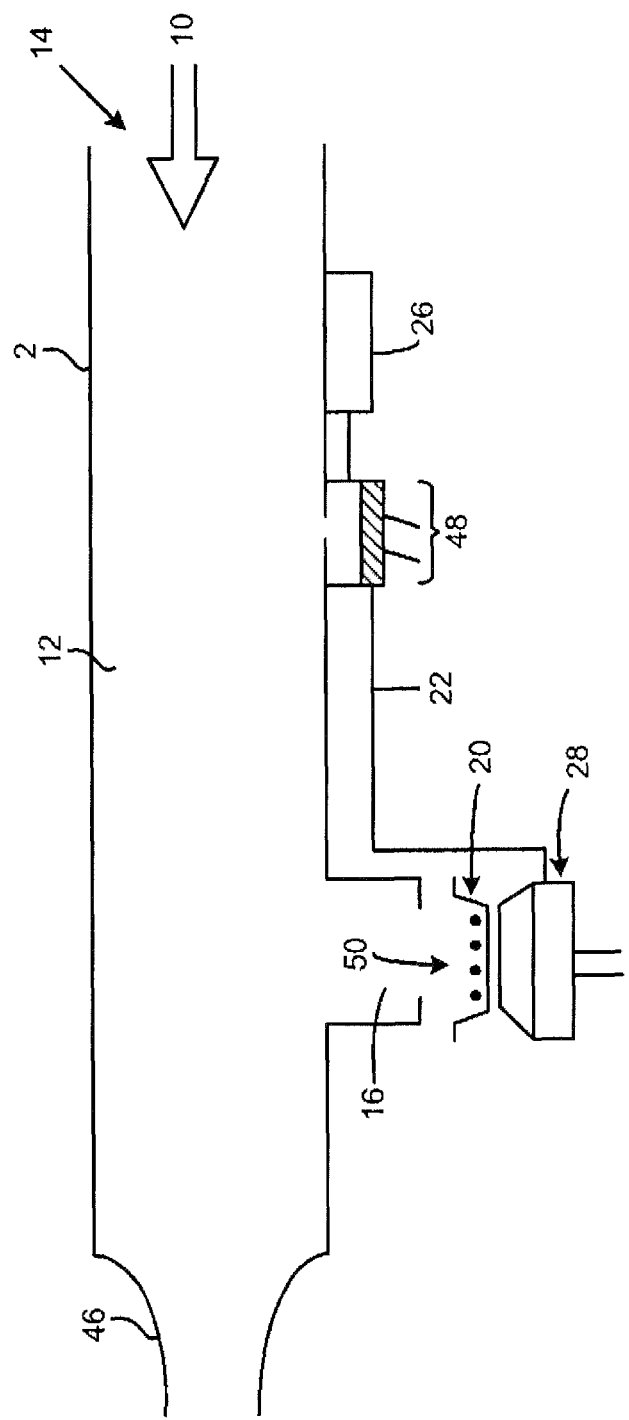
FIG. 1 is a cross-sectional side view of an inhaler, in accordance with a first exemplary embodiment of the present invention.

FIG. 1 is a cross-sectional side view of an inhaler 2, in accordance with a first exemplary embodiment of the present invention. As shown in FIG. 1, air 10, or other fluid, enters the airflow passageway 12. The flow of air 10 may be triggered by respiratory activity of a patient inhaling on the device 2. The flow of air 10 moves from a distal end 14 of the inhaler 2, through the passageway 12, to a proximate end 46 of the inhaler 2. A mouthpiece may be provided for the patient at the proximate end 46 of the inhaler 2, from which the patient inhales.

A vibrating mechanism 28 is provided proximate to a third opening 16 in the inhaler 2. The vibrating mechanism 28 may include, but is not limited to, a piezoelectric element, an ultrasonic acoustic transducer, or any other electro/mechanical vibratory mechanism. A container 20 is provided proximate to the vibrating mechanism 28. The container 20 and vibrating mechanism 28 are at least sufficiently proximate to allow the container 20 to be vibrated by the vibrating mechanism 28. The container 20 may be a blister capsule such as the blister capsule described in U.S. Pat. No. 7,318,434 assigned to MicroDose Technologies, Inc, the disclosure of which is incorporated herein in its entirety. The container 20 contains a powder 50 to be disaggregated by the vibrating mechanism 28. The inhaler 2 may be structured to allow the container 20 to be discarded and replaced after each use of the inhaler 2.

Control circuitry 48 is contained in the inhaler 2. The control circuitry may be embodied as an application specific integrated circuit chip and/or other integrated circuit chip. The control circuitry 48 may take the form of a microprocessor, or discrete electrical and electronic components and may include one or more elements remotely connected to the inhaler 2. The control circuitry 48 determines an amount of power to be supplied from a power source 26 to the vibrating mechanism 28. The control circuitry may control amplitude and/or frequency of actuating power to be supplied from the power source 26 to the vibrating mechanism 28, which will impact a level to which the vibrating mechanism 28 vibrates. The actuating power may be provided by an electrical connection 22 between the vibrating mechanism 28 and the power source 26, with the control circuitry 48 at least partially controlling the electrical connection 22. The electrical connection 22 may include a circuit device that transforms a DC power provided by the power source 26 to AC power for the vibrating mechanism 28, which circuit devices are known to those having ordinary skill in the art of circuit design.

The vibrating mechanism 28 may include a piezoelectric element 28 made of a material that has a high-frequency, and preferably, ultrasonic resonant vibratory frequency (e.g., about 15 to 100 MHz), and is caused to vibrate with a particular frequency and amplitude depending upon the frequency and/or amplitude of excitation electricity applied to it. Examples of materials that can be used to create the piezoelectric element include quartz and polycrystalline ceramic materials (e.g., barium titanate and lead zirconate titanate). Advantageously, vibrating the piezoelectric element at ultrasonic frequencies minimizes noise with vibrating the piezoelectric element at lower (i.e., below ultrasonic) frequencies.

Figure 2:
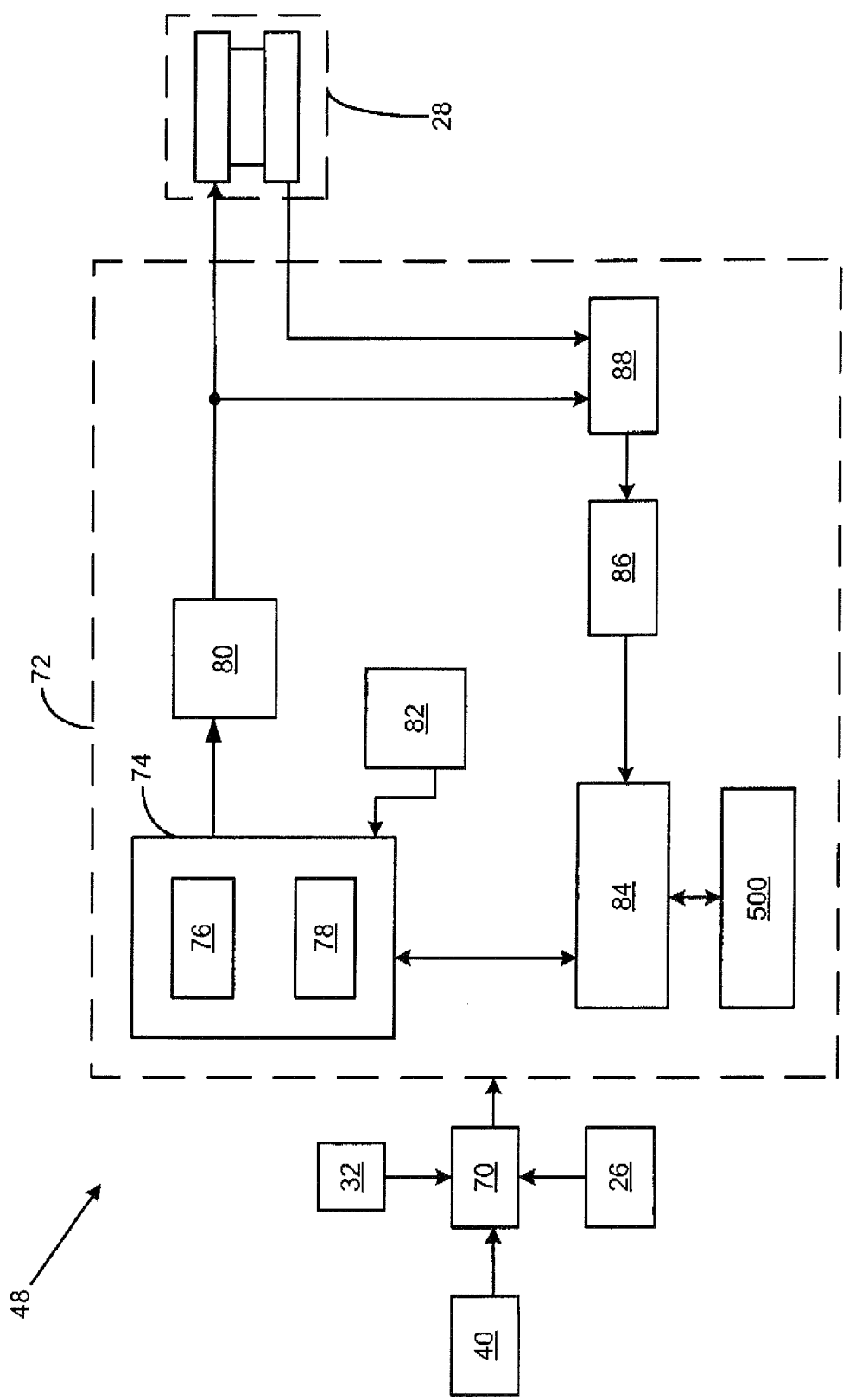
FIG. 2 is an illustration of a block diagram of the vibration control system for the inhaler shown in FIG. 1, in accordance with the present invention first exemplary embodiment of the present invention.

FIG. 2 is an illustration of a block diagram of the vibration control system for the inhaler shown in FIG. 1, in accordance with the present invention first exemplary embodiment of the present invention. As will be understood by those skilled in the art, although the functional components shown in FIG. 1 are directed to one possible physical embodiment of the present invention. The components of FIG. 1 could be appropriately modified, altered, and or rearranged without departing from the scope of the present invention and other inhaler configurations may benefit from the vibration control system described herein.

Control circuitry 48 may include am actuation controller 70 and a control subsystem 72. The actuation controller 70 may include a switching mechanism for permitting actuating power to be supplied from the power source 26 to the control subsystem 72 depending upon the signals supplied to it from an airflow sensor 40. The airflow sensor 40 would limit ignition of the vibrating mechanism 28 to occasions when someone is inhaling from the proximate end 46 of the inhaler 2. A toggle switch 32 may also be provided with the control circuitry 48, to make sure the power source 26 is drained due to ambient airflow. In other words, controller 70 permits actuating power to be supplied from the power source 26 to the control subsystem 72 when the toggle switch 32 is set to the "ON" position and the airflow sensor 40 supplies a signal to the actuation controller 70 that indicates that inhalation is occurring through the airflow passageway 12. However, the actuation controller 70 does not permit actuating power to flow from the power source 26 to the system 72 when either the toggle switch 32 is set to "OFF" or the signal supplied to the controller 70 from the airflow sensor 40 indicates that inhalation is not taking place through the airflow passageway 12.

When the actuation controller 70 first permits actuating power to be supplied from the power source 26 to the control subsystem 72, the control subsystem 72 may enter an initialization state wherein a controllable circuit 74 for supplying a predetermined frequency and amplitude of actuating power is caused to generate control signals. The control signals cause a pump circuit 80 to transmit an initial desired frequency and amplitude of actuating power, based upon stored values thereof stored in an initialization memory 82. The controllable circuit 74 may include a frequency sweep generator 76 and a frequency generator 78. The signals generated by the controllable circuit 74 may be supplied to charge the pump circuit 80 to cause the pump circuit 80 to supply the vibrating mechanism 28 with actuating power as specified by the control signals.

Preferably, the initial frequency and amplitude of actuating electricity supplied to the vibrating mechanism 28 is precalibrated to cause the vibrating mechanism 28 to be driven to a steady state condition. As will be appreciated by those skilled in the art, substantially maximum transfer of vibratory power from the vibrating mechanism 28 to the powder 50 in the container 20 takes place when the piezoelectric element 90 is driven to vibrate at an approximately steady state. It has been found that this results in significant disaggregation and suspension of the powder 50 from the container 20 into the air to be inhaled by the user. However, when the container 20 or powder 50 is placed on the vibrating mechanism 28, the weight and volume of the container 20, with the weight, volume, and particular size of the powder 50 to be disaggregated, can change the vibration characteristics of the vibrating mechanism 28, and cause the vibrating mechanism 28 to vibrate at something other than its resonant frequency. The resulting frequency can cause reduced vibratory energy transfer to the powder 50 from the vibrating mechanism 28 and, thereby, lessen the efficiency of the vibrating mechanism 28 in disaggregating and suspending the powder 50 in the air inhaled by the user.

In the control circuitry 48, once steady state occurs, the supply signal from the pump circuit 80 is stopped. The vibrating mechanism 28 should continue to vibrate due to its momentum. If the vibrating mechanism 28 includes a piezoelectric element, continued vibration will induce a voltage due to the piezoelectric effect, which can be measured by a sensor 88, such as a voltmeter, in the first few cycles after the supply signal from the pump circuit 80 is stopped. The voltage observed should be directly proportional to the displacement of the piezoelectric element 90.

The frequency sweep generator 76 and the frequency generator 78 systematically generate control signals indicative of many different amplitudes and frequencies of electricity for being supplied to the vibrating mechanism 28 by the pump circuit 80. As the frequency generator 78 "cycles through" different frequencies and amplitudes, and the signal supplied by the pump circuit 80 is intermittently stopped, the instantaneous continued vibration characteristics of the vibrating mechanism 28 for each of these different frequencies and amplitudes are detected by the sensor 88, which transmits this information to a peak power detector 86. The peak power detector 86 analyzes the output of the sensor 88 and signals a sample and hold feedback controller 84 when the power transfer characteristics are at a detected local maxima. The sample and hold feedback controller 84 correlates these local maxima with the frequencies and amplitudes commanded by the controllable circuit 74 to be supplied to the vibrating mechanism 28. The sample and hold feedback controller 84 may store information in a memory 500 in communication with the sample and hold feedback controller 84.

After the frequency sweep generator 76 and the frequency generator 78 has finished sweeping through the frequencies and amplitudes of power supplied to the vibrating mechanism 28, the sample and hold feedback controller 84 causes the controllable circuit 74 to cycle through the frequencies and amplitudes of power that resulted in local maxima, and determine which of these frequencies and amplitudes results in a detected optimal power transfer characteristics through the vibrating mechanism 28.

In operation, the container 20 may be punctured and engaged with the surface of the vibrating mechanism 28 in the manner described previously. The toggle switch 32 is placed in the "ON" position and the user inhales air through the proximate end 46. The inhalation of air 10 is sensed by the airflow sensor 40 and is signaled to the actuation controller 70, which causes power to be supplied to the control subsystem 72. The control subsystem 72 then adjusts the amplitude and frequency of actuating power supplied to the vibrating mechanism 28 until optimized for optimal disaggregation and suspension of the powder 50 from the container 20 into the air stream.

FIG. 3 is a flowchart 200 illustrating a method of providing the abovementioned dry powder inhaler 2, in accordance with the first exemplary embodiment of the invention. It should be noted that any process descriptions or blocks in flow charts should be understood as representing modules, segments, portions of code, or steps that include one or more instructions for implementing specific logical functions in the process, and alternate implementations are included within the scope of the present invention in which functions may be executed out of order from that shown or discussed, including substantially concurrently or in reverse order, depending on the functionality involved, as would be understood by those reasonably skilled in the art of the present invention.

As is shown by block 202, a vibrating mechanism 28 is driven to an approximate steady state using a first power input. The first power input is removed, wherein a vibration of at least a portion of the vibrating mechanism 28 continues (block 204). The vibration of the vibrating mechanism 28 is sensed after the voltage input is removed (block 206). The steps of driving, removing, and sensing with a plurality of different power inputs are repeated (block 208). The voltage input that produced a largest sensed vibration is determined (block 210). The vibrating mechanism 28 is positioned to disaggregate the dry powder 50 (block 212).

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

What is claimed is:

1. A method of providing feedback control in a dry powder inhaler, the method comprising the steps of:

driving a vibrating mechanism to an approximate steady state using a first power input;

removing the first power input, wherein a vibration of at least a portion of the vibrating mechanism continues;

sensing the vibration of the vibrating mechanism after the voltage input is removed;

repeating the steps of driving, removing, and sensing with a plurality of different power inputs, wherein the plurality of different power inputs differ according to frequency;

determining which of the voltage inputs produced a largest sensed vibration; and positioning the vibrating mechanism to disaggregate a dry powder.

2. The method of claim 1, wherein the step of positioning precedes the step of removing.

3. The method of claim 1, wherein the step of driving a vibrating mechanism further comprises the step of driving a piezoelectric transducer to vibrate.

4. The method of claim 3, wherein the step of sensing the vibration further comprises detecting an output voltage from the piezoelectric transducer.

5. The method of claim 1, wherein the plurality of different power inputs differ according to frequency.

6. The method of claim 1, wherein the plurality of different power inputs differ according to magnitude.

7. The method of claim 1, further comprising the step of correlating the plurality of different power inputs with a plurality of different vibrations sensed.

8. A dry powder inhaler, comprising:
a vibrating mechanism;
a supply of a dry powder operatively coupled to the vibrating mechanism;
a power source in communication with the vibrating mechanism, the power source having an intermittent power supply signal supplied to the vibrating mechanism;
an airflow sensor for sensing when a user is inhaling;
an actuation controller in communication with the airflow sensor for permitting actuating power to be supplied from the power source to the vibrating mechanism;
a vibrating mechanism sensor in communication with the vibrating mechanism, wherein the vibrating mechanism sensor is positioned to measure an instantaneous continued vibration characteristic of vibrating mechanism during a stop interval of the intermittent power supply signal; and
a feedback control in communication with the vibrating mechanism sensor and the power source, whereby the feedback control controls power delivered to the vibrating mechanism.

* * * * *

UNITED STATES PATENT AND TRADEMARK OFFICE
CERTIFICATE OF CORRECTION

Page 1 of 1

PATENT NO. : 8,439,033 B2
APPLICATION NO. : 12/246208
DATED : May 14, 2013
INVENTOR(S) : Gumaste et al.

It is certified that error appears in the above-identified patent and that said Letters Patent is hereby corrected as shown below:

On the Title Page, item (56), add reference "guidance for Industry- Nonclinical Safety Evaluation of Drug Combinations", U.S. Department of health and Human Services, Food and Drug Administration, Center for Drug Evaluation and Research (CDER), Pharmacology and Toxicology, January 2005"

In the Claims:

Claim 8, Col. 9, line 18 "operativcly" should be "operatively"

Signed and Sealed this
Twenty-first Day of October, 2014

Michelle K. Lee
*Deputy Director of the United States Patent and Trademark Office*